(12) United States Patent
Brigatti

(10) Patent No.: US 6,869,912 B2
(45) Date of Patent: Mar. 22, 2005

(54) BIOCIDAL COMPOSITION

(76) Inventor: John Murray Brigatti, 47 Elvire Street, Waterman, Western Australia (AU), 6020

( * ) Notice: Subject to any disclaimer, the term of this patent is extended or adjusted under 35 U.S.C. 154(b) by 0 days.

(21) Appl. No.: 10/380,307

(22) PCT Filed: Aug. 10, 2001

(86) PCT No.: PCT/AU01/00987

§ 371 (c)(1),
(2), (4) Date: Mar. 13, 2003

(87) PCT Pub. No.: WO02/22507

PCT Pub. Date: Mar. 21, 2002

(65) Prior Publication Data

US 2003/0187066 A1 Oct. 2, 2003

(30) Foreign Application Priority Data

Sep. 13, 2000  (AU) .............................................. PR0087

(51) Int. Cl.[7] .............................................. A01N 59/20
(52) U.S. Cl. ...................................... 504/152; 504/190
(58) Field of Search ................................. 504/152, 190

(56) References Cited

U.S. PATENT DOCUMENTS

| | | | | |
|---|---|---|---|---|
| 1,785,472 A | * | 12/1930 | Adler | .......................... 424/695 |
| 3,846,460 A | | 11/1974 | Fite, Jr. | .................... 260/438.1 |
| 3,906,036 A | * | 9/1975 | Dirks et al. | .................. 560/243 |
| 5,632,904 A | * | 5/1997 | Samad et al. | ................ 210/764 |
| 6,093,422 A | * | 7/2000 | Denkewicz, Jr. et al. | ... 424/618 |
| 6,458,335 B1 | * | 10/2002 | Lemaitre et al. | ......... 423/419.1 |

FOREIGN PATENT DOCUMENTS

| | | |
|---|---|---|
| DD | 291322 | 6/1991 |
| JP | 47/023369 | 7/1972 |
| JP | 01/307493 | 12/1989 |
| JP | 04/018005 | 1/1992 |
| RO | 94390 | 4/1988 |
| WO | WO 99/37584 | 7/1999 |
| WO | WO 00/39837 | 7/2000 |

OTHER PUBLICATIONS

Hirai et al.; *Preparation of fine particles using emulsified liquid membranes*; (Abstract of paper printed in Proceedings of ISEC '96, Mar. 19–23, 1996, Melbourne, Australia); pp. 1661–1666.

* cited by examiner

Primary Examiner—S. Mark Clardy
(74) Attorney, Agent, or Firm—James Creighton Wray; Meera P. Narasimhan

(57) ABSTRACT

A biocidal composition comprising copper (II) oxalate.

39 Claims, No Drawings

BIOCIDAL COMPOSITION

This application claims the benefit of Australian Provisional Application No. PR 0087 filed Sep. 13, 2000 and PCT/AU01/00987 filed Aug. 10, 2001.

FIELD OF THE INVENTION

The present invention relates to a biocidal composition. In particular, the biocidal composition of the present invention is intended for use in water bodies. The present invention further relates to a method for production of a biocidal composition, and a method for application thereof to a water body.

BACKGROUND ART

The biocidal properties of copper (II) salts are known. For example copper (II) sulphate pentahydrate is widely used as an agricultural fungicide, algicide, bactericide and herbicide. Further, it is known to apply the biocidal properties of copper (II) salts to treat water bodies. However, at elevated levels, copper (II) salts generally, and copper (II) sulphate pentahydrate in particular, are toxic to humans. On the other hand, if the levels of copper (II) salts are too low the biocidal effect is compromised.

Accordingly, when using a copper (II) salt to treat a body of water, it is extremely important that the copper (II) ions be evenly distributed throughout the body of water, at an appropriate concentration. A concentration of copper (II) ions between 2 and 10 parts per million is effective in controlling most bacteria and algae. Substantially lower levels of 0.5 to 1 parts per million are effective in inhibiting the growth of some susceptible species. Concentrations of copper (II) ions of up to 2 parts per million are not toxic to almost all plants and animals over extended periods of time. Levels of 10 parts per million are tolerated by most plants and animals over relatively short periods of time.

It is one object of the present invention to provide a biocidal composition that facilitates the provision of appropriate levels of copper (II) throughout a water body. It is a further object of the present invention to provide a method for production of the biocidal agent, and a method for application of the biocidal agent to a water body.

The preceding discussion of the background to the invention is intended to facilitate an understanding of the present invention. However, it should be appreciated that the discussion is not an acknowledgement or admission that any of the material referred to was part of the common general knowledge in Australia as at the priority date of the application.

Throughout the specification, unless the context requires otherwise, the word "comprise" or variations such as "comprises" or "comprising", will be understood to imply the inclusion of a stated integer or group of integers but not the exclusion of any other integer or group of integers.

Throughout the specification, unless the context requires otherwise, the phrase "water body" or variations such as "water bodies" will be understood to include bores, wells, water pumps, reservoirs, dams, lakes, water pipes, reticulation systems, and the like.

DISCLOSURE OF THE INVENTION

In accordance with the present invention there is provided a biocidal composition for the treatment of a water body, the biocidal composition comprising copper (II) oxalate.

Preferably, the biocidal composition comprises an aqueous suspension of copper (II) oxalate particles. Preferably still, the copper (II) oxalate particles are predominantly of a size below 25 $\mu$m.

Preferably still, the copper (II) oxalate particles are predominantly of a size below 15 $\mu$m.

Further and still preferably, the copper (II) oxalate particles are predominantly of a size below 10 $\mu$m.

Preferably, the biocidal composition further comprises a buffering agent. Preferably still the buffering agent buffers the biocidal composition such that the pH is maintained with in the approximate range of 6 to 8. In a preferred form of the invention, the buffering agent comprises a carbonic acid/hydrogen carbonate buffer.

In accordance with the present invention there is further provided a method for the preparation of a biocidal composition, the method comprising the steps of:

dissolving a copper (II) salt in a first portion of water to form an aqueous solution containing copper (II) ions;

at least partially dissolving oxalic acid in water to form an aqueous solution/suspension containing oxalic acid/oxalate ions;

mixing the solution containing copper (II) ions with the solution/suspension containing oxalic acid/oxalate ions to form a mixture containing copper (II) ions and oxalate ions; and inducing the formation of or allowing the spontaneous formation of solid copper (II) oxalate, leaving a residual solution.

Preferably still, the copper (II) oxalate particles are predominantly of a size below 25 $\mu$m.

Preferably still, the copper (II) oxalate particles are predominantly of a size below 15 $\mu$m.

Further and still preferably, the copper (II) oxalate particles are predominantly of a size below 10 $\mu$m.

The mixture containing copper (II) ions and oxalate ions may be agitated.

Conveniently, the copper (II) salt is provided in the form of copper (II) sulphate. In a specific form of the invention, the copper (II) salt is provided in the form of copper (II) sulphate pentahydrate.

Conveniently, the oxalic acid is provided in the form of oxalic acid dihydrate.

After the step of mixing the solution containing copper (II) ions with the solution containing oxalic acid/oxalate ions, the method may comprise the step of:

adding an alkaline agent to the mixture containing copper (II) ions and oxalate ions.

Preferably, sufficient alkaline agent is added to at least substantially neutralise any acid. Conveniently, the alkaline agent is sodium carbonate.

After the step of mixing the solution containing copper (II) ions with the solution containing oxalic acid/oxalate ions, the method may comprise the step of:

adding a buffering agent to the mixture containing copper (II) ions and oxalate ions.

Preferably, the buffering agent buffers the mixture such that the pH is maintained with in the approximate range of 6 to 8. In a highly preferred form of the invention, the buffering agent comprises a carbonic acid/hydrogen carbonate buffer, and the step of adding the alkaline agent also constitutes the step of adding the buffering agent.

After the step of inducing the formation of or allowing the spontaneous formation of solid copper (II) oxalate, the method of the present invention may comprise the additional steps of:

inducing the solid copper (II) oxalate to settle or allowing the solid copper (II) oxalate to settle from the residual solution; and decanting at least a portion of the residual solution from the solid copper (II) oxalate.

Preferably, where the solid copper (II) oxalate is allowed to settle from the residual solution, the copper (II) oxalate is allowed to settle from the residual solution for a period of between approximately 16 to 24 hours.

Where the method of the present invention comprises the step of decanting at least a portion of the residual solution from the solid copper (II) oxalate, the method may further comprise the step of:

adding water to the solid copper (II) oxalate.

In one form of the invention, the solution containing oxalic acid/oxalate ions is added to the solution containing copper (II) ions in portions. In a highly specific form of the invention, the aqueous solution containing oxalic acid/oxalate ions is added to the solution containing copper (II) ions in three approximately equal portions.

Preferably, the concentrations and volumes of the solution containing oxalic acid/oxalate ions and the solution containing copper (II) ions are such that approximately equimolar amounts of oxalic acid/oxalate and copper (II) ions are combined.

Preferably, the method of the present invention is performed at a temperature between about 10 and 40° C. Preferably still, the method of the present invention is performed at a temperature between about 15 and 35° C. In a specific form of the invention, the method is performed at a temperature between about 20 and 30° C. In a highly specific form of the invention, the method is performed at approximately 25° C.

Conveniently, the method is performed at room temperature.

Preferably, the solution containing copper (II) ions contains between about 0.1 and 1.5 molL$^{-1}$ copper (II) ions. Preferably still, the solution containing copper (II) ions contains between about 0.6 and 1.2 molL$^{-1}$ copper (II) ions. In a highly preferred form of the invention, the solution containing copper (II) ions contains between about 0.7 and 1.1 molL$^{-1}$ copper (II) ions. Preferably still, the solution containing copper (II) ions contains approximately 1.1 molL$^{-1}$ copper (II) ions.

Preferably, the solution containing oxalic acid/oxalate ions contains between about 0.1 and 2.0 molL$^{-1}$ oxalic acid/oxalate ions. Preferably still, the solution containing oxalic acid/oxalate ions contains between about 0.6 and 1.5 molL$^{-1}$ oxalic acid/oxalate ions. In a highly preferred form of the invention, the solution containing oxalic acid/oxalate ions contains between about 0.8 and 1.3 molL$^{-1}$ oxalic acid/oxalate ions. Preferably still, the solution containing oxalic acid/oxalate ions contains approximately 1.1 molL$^{-1}$ oxalic acid/oxalate ions.

In accordance with the present invention there is provided a method for treatment of a water body having a depth, the method comprising the steps of:

introducing a biocidal composition comprising copper (II) oxalate into the water body at a predetermined dosage; and allowing the copper (II) oxalate to settle substantially through the depth of the water body, allowing such to dissolve and thereby producing a biocidal concentration of copper (II) ions throughout the depth of the water body.

Where the water body is a pond or lake, the predetermined dosage is largely dependant on the degree of bio-fouling of the water body. However, typically, the dose is between about 0.04 mol to 0.16 mol of copper (II) per 100 m$^3$ of water.

Where the water body is a well or bore, the predetermined dosage is largely dependent on the volume of the water body. However, typically, the dose is between about 0.04 mol to 0.16 mol of copper (II) per m$^3$ of water.

The time for which the biocidal composition is allowed to settle depends on the depth of the water body. However, preferably, the settling time exceeds four hours. Preferably still, the settling time is between 8 and 16 hours.

Preferably, where the water body is a well or bore, the method further comprises the step of:

removing excess copper (II) oxalate from the water body to ensure that the water is safe for any intended use.

The biocidal composition may be diluted before being introduced into the water body.

BEST MODE(S) FOR CARRYING OUT THE INVENTION

The best mode for performing the invention presently known to the applicant will now be described. It should be noted that the following description does not limit the scope of the invention as described in the preceding disclosure.

A biocidal composition is prepared by first dissolving a copper (II) salt, in the form of copper (II) sulphate pentahydrate in a first portion of water to form an aqueous solution containing copper (II) ions. Three portions of oxalic acid dihydrate are in turn substantially dissolved in three portions of water to produce three portions of a suspension/solution containing oxalic acid/oxalate ions. The total oxalic acid dihydrate dissolved corresponds to an approximately equimolar amount to the copper (II) sulphate pentahydrate. The solution containing copper (II) ions contains approximately 1.1 molL$^{-1}$, and each of the portions of the suspension/solution containing oxalic acid/oxalate ions is approximately 1.1 molL$^{-1}$ oxalic acid/oxalate. The solutions are at room temperature.

The three portions of the suspension/solution containing oxalic acid/oxalate ions are sequentially added to the solution containing copper (II) ions and the mixture containing copper (II) ions and oxalate ions stirred for five to ten minutes, whilst copper (II) oxalate is formed, and acid released into the residual solution. An alkaline and buffering agent, in the form of sodium carbonate, is added portion wise to the mixture to at least substantially neutralise the released acid and buffer the biocidal composition to a pH of between 6 and 8.

Solid copper (II) oxalate is allowed to settle from the residual solution for between 16 and 24 hours before part of the residual solution is decanted therefrom. The solid copper (II) oxalate is then resuspended in water such that the total volume is 80 L, thereby reducing the amount of residual sodium and sulphate ions present in the suspension.

The copper (II) oxalate particles so formed predominantly have sizes below 10 μm. Virtually no particles of copper (II) oxalate in excess of 25 μm in size are present.

The biocidal composition, comprising the suspension of copper (II) oxalate particles, may then be diluted and introduced into a water body, such as a bore or well. The biocidal composition may be introduced into a bore from the surface between the bore casing and the pump column, or through an access tube attached to the pump column, terminating in the water above the pump. The bore should be disengaged when the biocidal composition is introduced, and not engaged for a period of at least four hours, and preferably 8 to 16 hours. The biocidal composition may be introduced into a water body such as a lake or dam by diluting such and spraying the diluted mixture over the surface of the pond or dam. Where the water body is a well or bore, and potable water is required, excess copper (II) should be flushed therefrom by discarding the first few thousand litres.

The solubility and particle size of the copper (II) oxalate particles present in the biocidal composition are such that (a) the copper (II) oxalate will settle to a sufficient extent to ensure distribution throughout the depth of the solution and (b) sufficient copper (II) oxalate will dissolve to give the required biocidal copper (II) concentration of between 5 and 8 parts per million.

EXAMPLES

The preparation of the biocidal composition and the efficacy of such will now be demonstrated with reference to the following examples. It should be noted that the description of the examples does not limit the scope of the invention as described in the preceding disclosure.

Example 1

Preparation of Biocidal Composition 16.6 kg (66.5 mol) of copper (II) sulphate pentahydrate was dissolved in approximately 50 L of water at room temperature in a reaction vessel to form an aqueous solution containing copper (II) ions. Three 2.85 kg (22.6 mol) portions of oxalic acid dihydrate were in turn substantially dissolved in three approximately 20 L portions of water at room temperature to produce three portions of a solution/suspension containing oxalic acid/oxalate ions.

The three 20 L portions of the solution/suspension containing oxalic acid/oxalate ions were sequentially added to the solution containing copper (II) ions and the mixture containing copper (II) ions and oxalate ions stirred for five to ten minutes, whilst copper (II) oxalate is formed, and acid released into the residual solution. Sodium carbonate (7.5 kg) is added portion wise to the mixture to substantially neutralise the released acid.

Solid copper (II) oxalate is then allowed to settle from the residual solution for between. 16 and 24 hours before part of the residual solution is decanted therefrom, to leave approximately 80 L of copper (II) oxalate suspension. The volume of the suspension is adjusted to 80 L with water, and the suspension homogenised and bottled.

The copper (II) oxalate particles so formed predominantly have sizes below 10 μm. Virtually no particles of copper (II) oxalate in excess of 25 μm in size are present.

Particle size analysis, using a Hiac/Royco 8000A Laser Extinction Counter of a typical batch of the biocidal preparation gave;

| | |
|---|---|
| Less than 5 μm | 46 percent |
| Between 5 and 10 μm | 38 percent |
| Between 10 and 15 μm | 14 percent |
| Between 15 and 25 μm | 2 percent |
| Greater than 25 μm | less than 1 percent. |

Example 2

Efficacy of Biocidal Composition: Copper Concentration

A portion of a biocidal composition prepared as described above was distributed on the surface of a measuring cylinder. The majority of the copper (II) oxalate particles were observed to settle throughout the water body, at a rate of 2–5 metres per hour. After standing for approximately four hours, samples were taken by pipette from various portions of the water body. The concentration of copper (II) ions in the water body was measured, by way of atomic absorption spectrophotometry, at between 5 and 8 parts per million.

Modifications and variation such as would be apparent to the skilled addressee are considered to fall within the scope of the present invention.

What is claimed is:

1. A biocidal composition for the treatment of a water body, the biocidal composition comprising an aqueous suspension of copper (II) oxalate particles, predominantly of a size below 25 μm, and a buffering agent, wherein the buffering agent maintains the biocidal composition at a substantially neutral pH.

2. A biocidal composition according to claim 1, wherein the copper (II) oxalate particles are predominantly of a size below 15 μm.

3. A biocidal composition according to claim 1, wherein the copper (II) oxalate particles are predominantly of a size below 10 μm.

4. A biocidal composition according to claim 1, wherein the buffering agent buffers the biocidal composition such that the pH is maintained with in the approximate range of 6 to 8.

5. A biocidal composition according to claim 1, wherein the buffering agent comprises a carbonic acid/hydrogen carbonate buffer.

6. A method for the preparation of a biocidal composition, the method comprising the steps of:

dissolving a copper (II) salt in a first portion of water to form an aqueous solution containing copper (II) ions;

at least partially dissolving oxalic acid in water to form an aqueous solution/suspension containing oxalic acid/oxalate ions;

maintaining the biocidal composition at a substantially neutral pH;

mixing the solution containing copper (II) ions with the solution/suspension containing oxalic acid/oxalate ions to form a mixture containing copper (II) ions and oxalate ions; and inducing the formation of or allowing the spontaneous formation of solid copper (II) oxalate particles predominantly of a size below 25 μm, and leaving a residual solution.

7. A method according to claim 6 wherein the copper (II) oxalate particles are predominantly of a size below 15 μm.

8. A method according to claim 6 wherein the copper (II) oxalate particles are predominantly of a size below 10 μm.

9. A method according to claim 6 wherein the mixture containing copper (II) ions and oxalate ions is agitated.

10. A method according to claim 6 wherein the copper (II) salt is provided in the form of copper (II) sulphate.

11. A method according to claim 10 wherein the copper (II) salt is provided in the form of copper (II) sulphate pentahydrate.

12. A method according to claim 6 wherein the oxalic acid is provided in the form of oxalic acid dihydrate.

13. A method according to claim 6 wherein after the step of mixing the solution containing copper (II) ions with the solution containing oxalic acid/oxalate ions, the method comprises the step of:

adding an alkaline agent to the mixture containing copper (II) ions and oxalate ions.

14. A method according to claim 13 wherein sufficient alkaline agent is added to at least substantially neutralise any acid.

15. A method according to claim 13 wherein the alkaline agent is sodium carbonate.

16. A method according to claim 6 comprising the step of, after mixing the solution containing copper (II) ions with the solution containing oxalic acid/oxalate ions:

adding a buffering agent to the mixture containing copper (II) ions and oxalate ions.

17. A method according to claim 16 wherein the buffering agent buffers the mixture such that the pH is maintained with in the approximate range of 6 to 8.

18. A method according to claim 16 wherein the buffering agent comprises a carbonic acid/hydrogen carbonate buffer, and the step of adding the alkaline agent also constitutes the step of adding the buffering agent.

19. A method according to claim 6, comprising the steps of, after inducing the formation of or allowing the spontaneous formation of solid copper (II) oxalate:

maintaining the biocidal composition at a substantially neutral pH;

inducing the solid copper (II) oxalate to settle or allowing the solid copper (II) oxalate to settle from the residual solution; and decanting at least a portion of the residual solution from the solid copper (II) oxalate.

20. A method according to claim 19 wherein the solid copper (II) oxalate is allowed to settle from the residual solution, the copper (II) oxalate is allowed to settle from the residual solution for a period of between approximately 16 to 24 hours.

21. A method according to claim 19 comprising the step of:

adding water to the solid copper (II) oxalate.

22. A method according to claim 6 wherein the solution containing oxalic acid/oxalate ions is added to the solution containing copper (II) ions in portions.

23. A method according to claim 22 wherein the aqueous solution containing oxalic acid/oxalate ions is added to the solution containing copper (II) ions in three approximately equal portions.

24. A method according to claim 6 wherein the concentrations and volumes of the solution containing oxalic acid/oxalate ions and the solution containing copper (II) ions are such that approximately equimolar amounts of oxalic acid/oxalate and copper (II) ions are combined.

25. A method according to claim 6 wherein the method is performed at a temperature between about 10 and 40° C.

26. A method according to claim 6 wherein the method is performed at room temperature.

27. A method according to claim 6 wherein the solution containing copper (II) ions contains between about 0.1 and 1.5 $molL^{-1}$ copper (II) ions.

28. A method according to claim 6 wherein the solution containing copper (II) ions contains approximately 1.1 $molL^{-1}$ copper (II) ions.

29. A method according to claim 6 wherein the solution containing oxalic acid/oxalate ions contains between about 0.1 and 2.0 $molL^{-1}$ oxalic acid/oxalate ions.

30. A method according to claim 6 wherein the solution containing oxalic acid/oxalate ions contains approximately 1.1 $molL^{-1}$ oxalic acid/oxalate ions.

31. A method for treatment of a water body having a depth, the method comprising the steps of:

introducing a biocidal composition comprising an aqueous suspension of copper (II) oxalate particles predominantly of a size below 25 $\mu$m into the water body at a predetermined dosage; and maintaining the biocidal composition at a substantially neutral pH, allowing the copper (II) oxalate to settle substantially through the depth of the water body, allowing such to dissolve and thereby producing a biocidal concentration of copper (II) ions throughout the depth of the water body.

32. A method according to claim 31 wherein the water body is a lake or pond, the predetermined dosage is between about 0.04 mol to 0.16 mol of copper (II) per 100 $m^3$ of water.

33. A method according to claim 31 wherein the water body is a bore, dam or well, the predetermined dosage is between about 0.04 mol to 0.16 mol of copper (II) per $m^3$ of water.

34. A method according to claim 31 wherein the settling time exceeds four hours.

35. A method according to claim 31 wherein the settling time is between 8 and 16 hours.

36. A method according to claim 31 comprising the step of:

removing excess copper (II) oxalate from the water body to ensure that the water is safe for any intended use.

37. A method according to claim 31 wherein the biocidal composition is diluted before being introduced into the water body.

38. A method according to claim 31, wherein the copper (II) oxalate particles predominantly of a size below 15 $\mu$m.

39. A method according to claim 31, wherein the copper (II) oxalate particles predominantly of a size below 10 $\mu$m.

* * * * *